United States Patent
Tsai (10) Patent No.: US 8,459,623 B2
(45) Date of Patent: Jun. 11, 2013

(54) POWDERED GRIP CLAMPING FORCE (75) Inventor: Kuo Tsing Tsai, Singapore (SG)

(73) Assignee: Instron Singapore Pte Ltd, Singapore (SG)

( * ) Notice: Subject to any disclaimer, the term of this patent is extended or adjusted under 35 U.S.C. 154(b) by 414 days.

(21) Appl. No.: 12/922,482

(22) PCT Filed: Apr. 14, 2009

(86) PCT No.: PCT/US2009/040442
§ 371 (c)(1),
(2), (4) Date: Sep. 14, 2010

(87) PCT Pub. No.: WO2009/131869
PCT Pub. Date: Oct. 29, 2009

(65) Prior Publication Data
US 2011/0018186 A1    Jan. 27, 2011

(30) Foreign Application Priority Data

Apr. 22, 2008  (SG) ................. 200803071-0

(51) Int. Cl.
*B23Q 3/00* (2006.01)
(52) U.S. Cl.
USPC .......................................... 269/134; 269/32
(58) Field of Classification Search
USPC ... 269/134, 32, 33, 24, 228, 95, 71; 254/93 R
See application file for complete search history.

(56) References Cited

U.S. PATENT DOCUMENTS

| 2,775,461 | A |   | 12/1956 | Ehrlich et al. |
| 2,850,926 | A |   | 9/1958 | Jobe |
| 3,069,761 | A | * | 12/1962 | Sommer ........................ 29/252 |
| 3,085,813 | A |   | 4/1963 | Sampson |
| 3,204,451 | A |   | 9/1965 | Cavanaugh et al. |
| 4,696,503 | A | * | 9/1987 | Collodel ........................ 294/207 |
| 6,578,821 | B2 | * | 6/2003 | Lasaroff et al. ............. 254/93 R |
| 6,609,705 | B1 | * | 8/2003 | Schindler et al. ............... 269/34 |
| 7,069,817 | B2 | * | 7/2006 | Wesch, Jr. .................... 81/57.16 |
| 7,293,765 | B2 | * | 11/2007 | Hooper ......................... 269/246 |
| 2011/0018186 | A1 | * | 1/2011 | Tsai ............................. 269/134 |

FOREIGN PATENT DOCUMENTS

| GB | 1077090 A | 7/1967 |
| SU | 1399115 A1 | 5/1988 |
| WO | 96/01724 A1 | 1/1996 |

OTHER PUBLICATIONS

ISR for PCT/US2009/040442 mailed Jan. 22, 2010.

* cited by examiner

*Primary Examiner* — Lee D Wilson
(74) *Attorney, Agent, or Firm* — Lowe Hauptman Ham & Berner, LLP (57) ABSTRACT

A powered grip that can engage and hold an item which includes a primary body member, an actuator dependent from the primary body member and a pair of spaced apart clamp jaws to move towards and away from each other. A force transmission mechanism is operatively located intermediate of the actuator and each of the clamp jaws to displace the clamp jaws relative to the primary body and that, through mechanical advantage, establishes a multiplication of the force of the actuator force at the clamp jaws. A force transmission mechanism geometry adjuster is provided to vary the spacing between the clamp jaws for any given operating force applied by the actuator, allow the pre-testing setting of the spacing between the jaws such that the range of force applied by the clamping jaws to the item to be tested is within a desired range.

34 Claims, 10 Drawing Sheets

POWDERED GRIP CLAMPING FORCE

RELATED APPLICATIONS

The present application is national phase of International Application Number PCT/US2009/040442 filed Apr. 14, 2009, and claims priority from, Singapore Application Number 200803071-0 filed Apr. 22, 2008.

FIELD OF INVENTION

This invention relates to adjustable clamping force powered grip and/or a mechanism to allow adjustment of the clamping force of a powered grip.

BACKGROUND

Powered grips are used in materials testing to hold specimens. The specimen's tensile strength and failure properties can be tested by applying a tensile or compression force to the specimen that may be held by two spaced apart grips. The clamping force that may be generated by conventional powered grips used in materials testing is usually determined by the force generated by the source of power. Typically this force is proportional to the operating pressure in a pneumatic or hydraulic cylinder of the powered grip. To obtain different clamping forces, the pressure is adjustable typically down to 10-20% of the maximum system pressure. In addition, for a typical grip design, the pneumatic or hydraulic force generated may be multiplied by a fixed factor (assuming no mechanical loss) or ratio so that the required clamping force is achieved. This can be achieved via a wedge or lever system that offers a mechanical advantage.

The most common way of multiplying the pneumatic or hydraulic force is to use a wedge mechanism, a lever arm, a gear mechanism or sometimes by using a pressure intensifier.

In these known designs, the multiplication force is designed to be relatively constant. For example, in an established design of a grip, the pneumatic piston has a wedge to push cam rods resulting in a multiplication of the piston force. The cam rods may then push against a lever which multiplies the force further. Various other mechanisms exist but central to such designs is that the force multiplication is relatively constant, cannot be user adjustable and is simply for the purpose of creating a compact grip design with sufficient clamping force.

In grippers used not for materials testing, but for specimen handling, a similar design approach is in use. Here, designs often result in a more variable clamping force but such a characteristic is seen as a disadvantage where a larger stroke results in lower gripping force.

Accordingly it is an object of the present invention to provide an adjustable clamping force powered grip and/or a mechanism to allow adjustment of the clamping force of a powered grip that addresses the above mentioned problems and/or desiderata or that will at least provide the public with a useful choice.

BRIEF DESCRIPTION OF THE INVENTION

Accordingly, in a first aspect the present invention broadly consists in a powered grip that can engage and hold an item, said grip comprising:
 a. a primary body member,
 b. an actuator dependent from said primary body member,
 c. a pair of spaced apart clamp jaws to move towards and away from each other and configured to clamp onto a said item to be clamped,
 d. a force transmission mechanism operatively located intermediate of said actuator and each of the clamp jaws of said pair of clamp jaws to displace said clamp jaws relative the primary body and that establishes a multiplication of the force of the actuator force at the clamp jaws by a factor greater than zero,
 e. force transmission mechanism geometry adjuster that can adjust the geometry of the force transmission mechanism in order to vary the spacing between the clamp jaws to thereby, for any given operating force applied by the actuator to the force transmission mechanism, allow the pre-clamping setting of the spacing between the jaws such that the range of force applied by the clamping jaws to the item to be clamped is within a desired range (such as for example a user determined range).

Preferably said actuator is one selected from (a) a piston and cylinder arrangement that is coupled to the transmission mechanism and displacement of the piston within the cylinder is effected by a fluid and (b) an electromechanical arrangement.

Preferably said clamp jaws are positioned spaced from each other and intermediate of which a said item to be clamped can be placed.

Preferably said force transmission mechanism includes at least one pivot point that remains fixed to said primary body and about which said force transmission mechanism can rotate in a manner to establish said multiplication of the force of the actuator force at the clamp jaws.

Preferably said force transmission mechanism comprises, for each clamp jaw, a lever member pivotally mounted relative the primary body and that is coupled to a said clamp jaw to, upon actuator effected movement about its pivot, move said clamp jaw relative the other said clamp jaw.

Preferably said force transmission mechanism, for each clamp jaw, also comprises a link beam that operatively couples the lever member with said piston, said link beam engaged to said lever member at a location to be able to apply a moment to said lever member about the pivot of the lever member that is transferred by said lever member as a clamp force to the clamp jaw.

Preferably for at least one of said clamp jaws, the clamp force is transferred to the clamp jaw via a jaw mount.

Preferably said force transmission mechanism, for each clamp jaw, also comprises a jaw mount.

Preferably the jaw mount is operatively engaged to the lever member and a respective clamp jaw.

Preferably said jaw mount is pivotally engaged to said lever member.

Preferably said jaw mount is pivotally engaged to said lever member at a location on the other side of the pivot to where said link beam is engaged.

Preferably said link beam is pivotally connected to said piston and said lever member.

Preferably said force transmission mechanism geometry adjuster is defined by said jaw mount that is adjustably mounted from said lever member in order to allow the distance between the clamp jaws to be varied, without movement of the lever member.

Preferably said force transmission mechanism geometry adjuster is defined by said jaw mount that is adjustable in size in order to allow the distance between the clamp jaws to be varied, without movement of the lever member.

Preferably said jaw mount comprises a first portion that remains secured to said lever member and a second position, held by said first portion in a movable relationship thereto.

Preferably said first portion and said second portion are threadingly engaged to each other, such that upon relative rotation, a linear displacement between the two occurs that thereby varies the spacing between the clamp jaws.

Preferably said force transmission mechanism geometry adjuster allows, for different spacing of clamp jaws at initial contact with an item to be clamped, the setting of the geometry of the force transmission mechanism in a condition so that, for a given operating pressure of the actuator, the multiplication of force remains within a range that corresponds to a desired range of clamping force.

Preferably the grip can be used for materials testing.

Preferably the force transmission mechanism achieved a force multiplication by being arranged to provide a mechanical advantage.

Preferably said force multiplication is by a factor greater than 1.

In a second aspect the present invention consists in a powered grip that can engage and hold an item, said grip comprising:
a. a primary body member,
b. an actuator dependent from said primary body member,
c. a pair of spaced apart clamp jaws mounted from said primary body in a manner to allow the distance between the clamp jaws to vary and each and configured to clamp onto a said item to be clamped,
d. a force transmission mechanism operatively located intermediate of said actuator and at least one of the clamp jaws of said pair of clamp jaws to displace said at least one clamp jaw relative the primary body to vary the distance between said clamp jaws and that establishes a multiplication of the force of the actuator force at the clamp jaws by a factor greater than zero,
e. force transmission mechanism geometry adjuster that can adjust the geometry of the force transmission mechanism in order to vary the distance between the clamp jaws to thereby, for any given operating force applied by the actuator to the force transmission mechanism, allow the pre-clamping setting of the spacing between the jaws such that the range of force applied to the item to be clamped between the clamping jaws is within a desired range.

Preferably said force transmission mechanism includes at least one pivot point that remains fixed to said primary body and about which said force transmission mechanism can rotate in a manner to establish said multiplication of the force of the actuator force at the at least one clamp jaw.

Preferably said force transmission mechanism comprises, for said at least one clamp jaw, a lever member pivotally mounted relative the primary body and that is coupled to said at least one clamp jaw to, upon actuator effected movement about its pivot, move said clamp jaw relative the other said clamp jaw.

Preferably said force transmission mechanism also comprises a link beam that operatively couples the lever member with said piston, said link beam engaged to said lever member at a location to be able to apply a moment to said lever member about the pivot of the lever member that is transferred by said lever member as a clamp force to the clamp jaw.

Preferably the clamp force is transferred to the at least one clamp jaw via a jaw mount.

Preferably said force transmission mechanism geometry adjuster is defined by said jaw mount that is adjustably mounted from said lever member in order to allow the distance between the clamp jaws to be varied, without movement of the lever member.

Preferably said force transmission mechanism geometry adjuster is defined by said jaw mount that is adjustable in size in order to allow the distance between the clamp jaws to be varied, without movement of the lever member.

Preferably the force transmission mechanism further comprises a combination of lever members mechanically linked to operatively couple said with actuator, said combination of lever members configured such as to be able to apply a moment to at least one of the lever members about the pivot of one of the lever members thereby transferring the clamp force to the clamp jaw.

Preferably the grip can be used in materials testing.

Preferably said combination of lever members comprises
a first lever member, one end which is operatively coupled to the actuator,
a second lever member, where at substantially one end is joined to the other end of the first lever member operatively coupled to the piston,
a third lever member having one end pivotally engaged to the second lever member,
a fourth lever member having one end pivotally engaged to the main body allowing the combination of lever members to apply a moment about said end, and the third lever member joined at its end to substantially midway of the fourth lever member,
wherein when the actuator actuates, the moment force generated from the combination of lever members operating mechanically applies a clamping force to the clamp jaw.

Preferably the first and second lever linked members are rigidly connected (preferably in a substantially perpendicular manner at their ends).

Preferably the end of the second lever linked member proximate the end connected to the first lever linked member, is coupled to the main body via a hinge joint.

Preferably wherein the second lever member is not in contact with the fourth lever member.

In still a further aspect the present invention consists in a powered grip for to engage and hold an item to be clamped, said grip comprising:
a. a primary body member,
b. an actuator dependent from said primary body member,
c. pair of spaced apart clamp jaw mounts to each receive a clamp jaw, the mounts to move towards and away from each other and configured to allow the clamp jaws, when mounted, to clamp onto a said item to be clamped,
d. a force transmission mechanism operatively located intermediate of said actuator and each of the clamp jaw mounts of said pair of clamp jaw mounts that can establish a multiplication of the force of the actuator force at the clamp jaws by a factor greater than zero,
e. force transmission mechanism geometry adjuster that can adjust the geometry of the force transmission mechanism in order to vary the spacing between the clamp jaw mounts to thereby, for any given operating force applied by the actuator to the force transmission mechanism, allow the pre-clamping setting of the spacing between the jaws such that the range of force applied by the clamping jaws to the item to be clamped is within a desired range.

In yet a further aspect the present invention consists in a method of clamping an item by utilising the power grip as herein before described wherein the clamp jaws are set a determined distance apart before the actuator is actuated to move the clamp towards each other.

Preferably the determined distance sets the free stroke of the clamp jaws and the force transmission mechanism and that will set the geometry of the force transmission mechanism upon initial clamping of the item.

In yet a further aspect the present invention consists in a powered grip for holding an item to be tensile tested and that may undergo a size reduction when under tension at the location where it is to held by the power grips, said grip comprising:
 a. a primary body member,
 b. an actuator dependent from said primary body member,
 c. a pair of spaced apart clamp jaws to move towards and away from each other and configured to clamp onto a said item to be clamped,
 d. a force transmission mechanism operatively located intermediate of said actuator and each of the clamp jaws of said pair of clamp jaws to displace said clamp jaws relative the primary body and that establishes a multiplication of the force of the actuator force at the clamp jaws by a factor greater than zero,
 e. force transmission mechanism geometry adjuster that can adjust the geometry of the force transmission mechanism in order to vary the spacing between the clamp jaws to thereby, for any given operating force applied by the actuator to the force transmission mechanism, allow the pre-clamping setting of the spacing between the jaws such that the range of force applied by the clamping jaws to the item to be clamped is within a desired range so that when the item, under tensile loading, decreases in size at the clamp jaws, the clamp jaws move to compensate for the size reduction and by virtue of the change in geometry of the force transmission mechanism, increase the clamping force.

This invention may also be said broadly to consist in the parts, elements and features referred to or indicated in the specification of the application, individually or collectively, and any or all combinations of any two or more of said parts, elements or features, and where specific integers are mentioned herein which have known equivalents in the art to which this invention relates, such known equivalents are deemed to be incorporated herein as if individually set forth.

As used herein the term "and/or" means "and" or "or", or both.

As used herein "(s)" following a noun means the plural and/or singular forms of the noun.

The term "comprising" as used in this specification means "consisting at least in part of". When interpreting statements in this specification which include that term, the features, prefaced by that term in each statement, all need to be present but other features can also be present. Related terms such as "comprise" and "comprised" are to be interpreted in the same manner.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

DETAILED DESCRIPTION OF THE INVENTION

Figure 1:
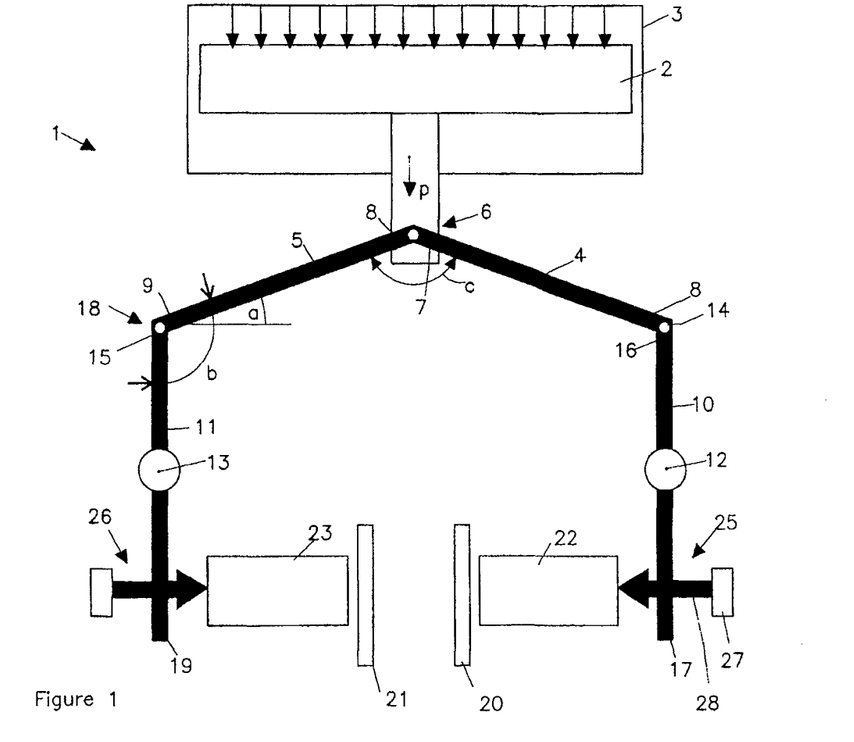
FIG. 1 is a schematic view of the powered grip of the present invention.
Figure 3A:
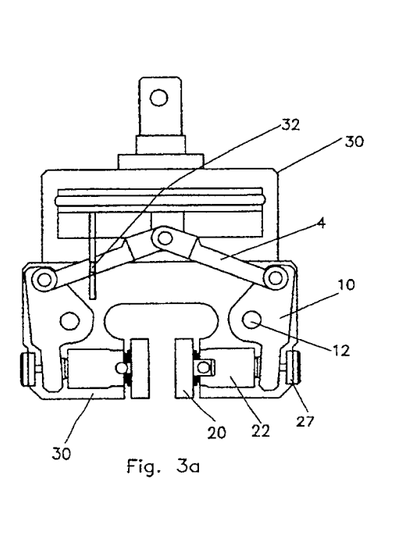
FIG. 3a is a side and partial hidden detailed view of the power grip of the present invention in a first position.
Figure 3B:
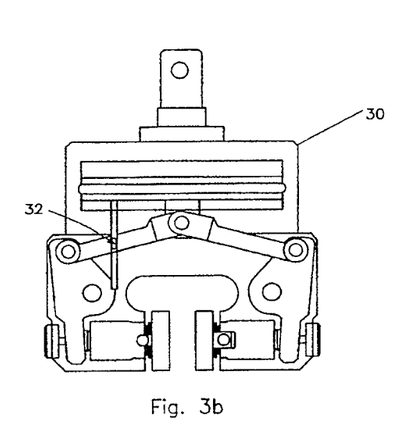
FIG. 3b is a view as per FIG. 4a but in a second position.
Figure 3C:
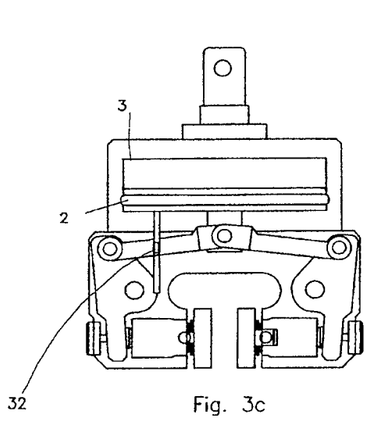
FIG. 3c is a view as per FIG. 4a but in a third position.
Figure 7A:
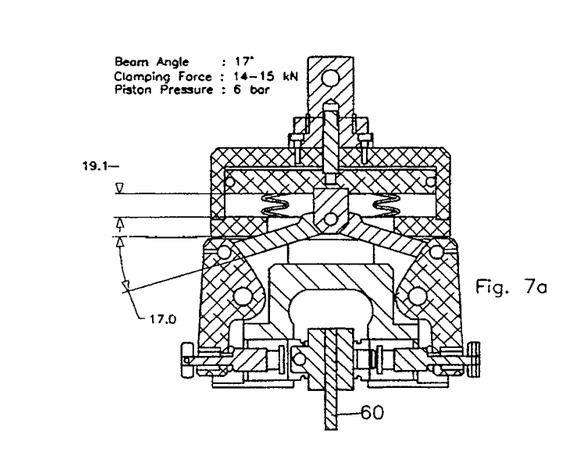
FIGS. 7a-7c illustrate the powered grip of the present invention in sectional view in various configurations.
Figure 7B:
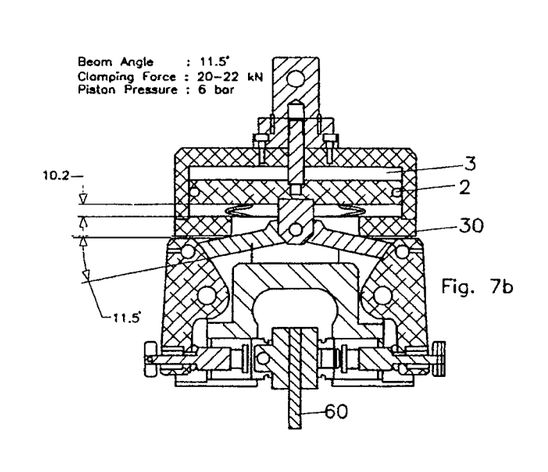
Figure 7C:
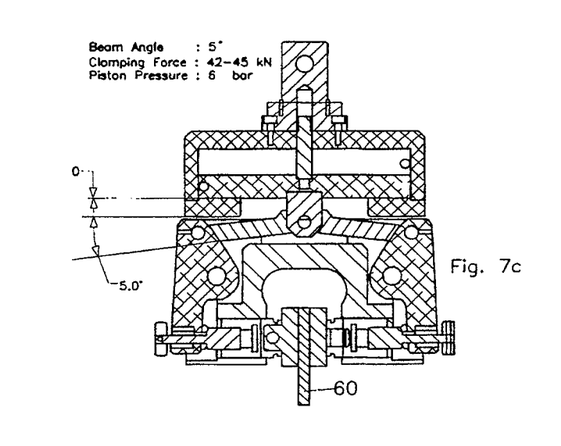
Figure 11:
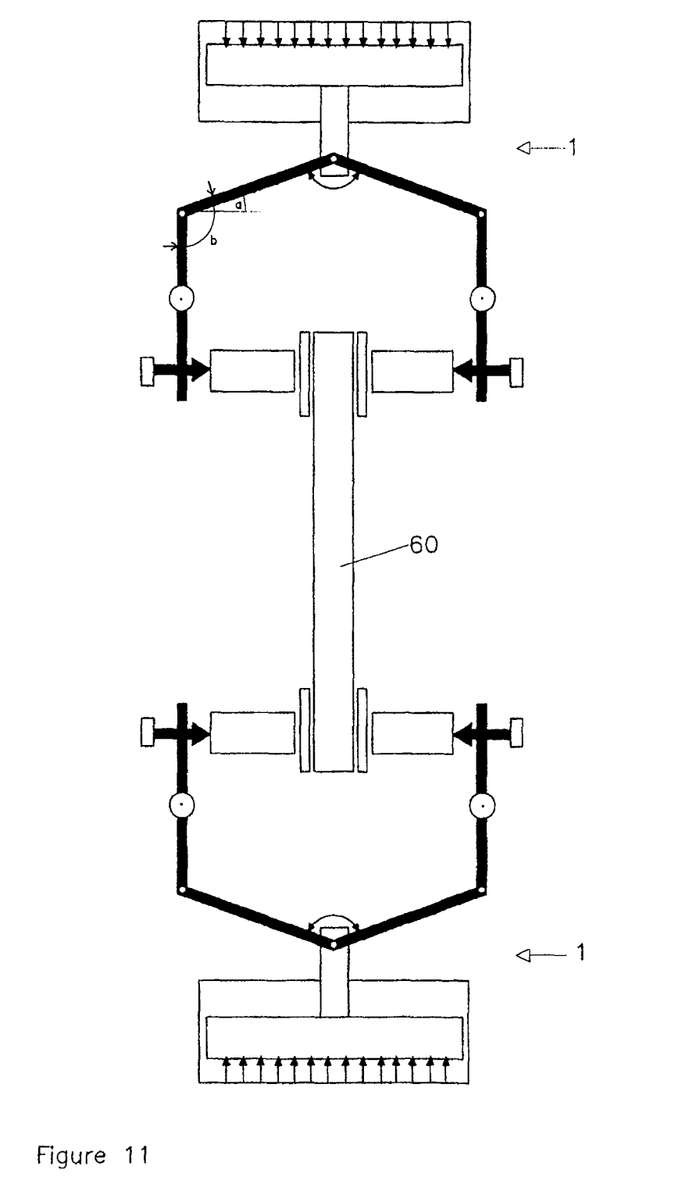
FIG. 11 is a schematic view of the assembly setup of the power grip for material testing.

The present invention is generally shown in FIG. 1 and more specifically in FIGS. 3a-3c and also in FIGS. 7a-7c. FIG. 11 shows the assembly setup of the power grip used for material testing. There are two grips 1 that can each hold a piece of material 60. The setup may only include one grip of the kind according to the present invention. The grip of the present invention may also be used for material handling. The grip 1 includes a main body 30 what holds a piston 2 within a cylinder 3. The piston 2 can be driven by a fluid such as a hydraulic fluid or compressed air. Other means of actuation such as by electromechanical means, for example, a motor with a drive screw, can also be utilised. Pressure control can occur remotely. Pressurisation of the fluid can occur remotely by fluid pressurising or intensifying devices that can deliver the fluid to the cylinder 3. Pressure in the cylinder can be controlled so as to remain at an appropriate level.

While reference to the embodiments described herein are made to a power grip relating to the tensile testing of a specimen, it is envisaged that compression testing or cyclic testing through zero load of a specimen may also be possible.

In one embodiment of the invention, the piston 2 acts (directly or indirectly) on two identical beams 4,5. A single hinged joint 6 may connect the piston with the beams. Preferably the piston 2 acts on the ends 7,8 of these two beams 4,5.

The two beams 4,5 are arranged in a bifurcated manner so that they are arranged at an angle to each other. The angle C between the two beams 4,5 is less than 180 degrees and greater than 90 degrees. At 180 degrees or greater, the grip will be in a locked position and cannot further apply an increasing clamping force. At 90 degrees or less, the clamping force multiplier from the piston will be less than unity and therefore ineffectual.

At or towards the other end 8 or 9 of each beam, each beam acts on a lever arm 10 or 11. This is preferably achieved via a hinged coupling 14 or 15. Intermediate of each lever arm between the distal ends 16 and 17 or 18 and 19 is a pivot point 12 or 13 of each lever arm. Its axis is parallel to that of the joint 6. The pivot point is generally centrally located between distal ends 16 and 17 or 18 and 19 for a force transfer ratio of 1:1 or could be located away from centre as design dictates. Away from the centre will have the effect of either changing (either increasing or decreasing) the clamping force multiplier by a factor of more than one or less than one, inversely decreasing or increasing the jaw face stroke. The pivot point may be defined by a pivot axle that is engaged to or fixed to the main body of the grip 1. The cylinder 3 also remains stationary to this main body 30.

The lever arms 10 and 11 each respectively act (directly or indirectly) on clamp jaws 20 and 21 preferably via jaw mounts 22 and 23. The jaw mount may be a simple pin and clevis or use of a "snap-on" jaw face design. This can allow for simple replacement of jaws so as to change their size, or change their shape. The jaw mounts can then move in jaw cylinders which are part of the main body 30. Between the clamp jaws 20 and 21 a specimen 60 may be placed that is to be held by the grip 1. A similar or other type of grip may be located to grip the specimen at another location to then allow the specimen to be subjected to a tensile force as the grip 1 and the other grip are moved apart.

The jaw mounts 22 and 23 each include an adjustment mechanism 25, 26. Alternatively, only one of the jaw mounts may include an adjustment mechanism. This mechanism allows the spacing of the clamp jaw 20 and 21 to be varied. This variation is independent of movement effected by the piston via the beams and the lever arms 10 and 11. This adjustment can be achieved by the user who is locating a specimen between the clamping jaws. So it can be done at the grip.

The adjustment mechanism may include a knob 27 that a user can turn, and that in turn will rotate an adjustment screw 28. The adjustment screw can be mounted to the lower arm so as to move relative thereto and so as to displace the clamp jaw relative the main body 30. The adjustment screw allows a pre-setting of the position of the jaws and geometry of the beam and lever arms. This then sets the initial configuration of the grip when the specimen is first engaged by the jaws.

Presetting the configuration in this manner can ensure that the grip geometry operates within a range that is desirable.

With reference to FIG. 1, the angle between the beam 5 and lever arm 11 is angle b. The angle between the beam 5 and a line passing through the hinged coupling 15 that extends perpendicular to the direction of travel of the piston 2 is angle a. Likewise the same angles exist in respect of the beam 4 and lever arm 10.

In use, a specimen is located between the clamp jaws 20 and 21. As the piston moves (eg in a direction downwards in respect of the orientation of FIG. 1 and as also shown in FIGS. 3a-3c) the thrust force (P) generated by the piston in a downward direction is translated to a thrust force in the axis of each of the beams 4,5. The thrust force in each of the beams can be calculated by the simple formula P/2sin(a). This thrust force in a beam (say beam 4) is transferred to the associated lever arm 10 as a moment acting at end 16 about pivot 12. This moment force is then reacted at the opposite end 17 of the lever arm 10, via the jaw mount 22 and clamp jaw 20 onto the specimen. Since the design of the grip is preferably symmetric, an equal clamping force is then applied on the specimen.

It would be noted that as the angle 'a' changes towards a smaller angle, P/2sin(a) increases. An important feature of the invention is setting of the range of the angle 'a' during any one specimen test. A secondary angle change also arises between the beam and the lever arm, the angle 'b'. As the angle deviates from 90 degrees, the moment from the force P/2sin (a) is reduced. Therefore, by designing the grip so that both appropriate range of angle 'b' and angle 'a' can be achieved, the range of the force multiplier can be tempered. The setting of the range that the angles 'a' and 'b' travel is determined by the adjustment mechanism setting which sets initial spacing of the clamp jaws. That, together with the size of the specimen, sets the clamp jaw stroke.

Figure 2:
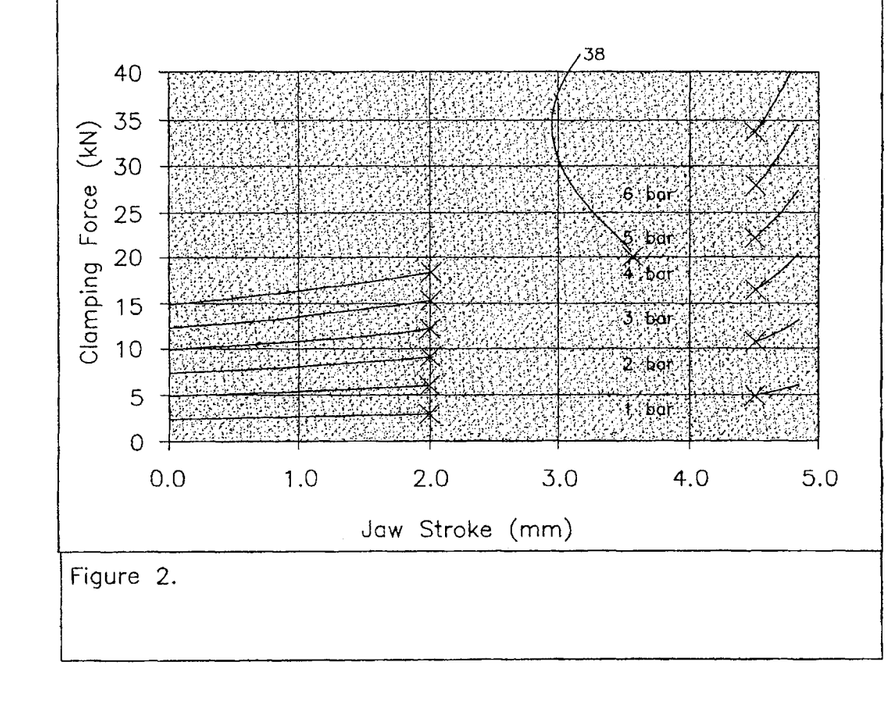
FIG. 2 is a graph illustrating clamp force and jaw stroke for various cylinder operating pressures.

In the preferred embodiment of a grip suitable for loading specimens in tension up to 10 kN, the typical range of clamping forces at different operating pressures is illustrated in FIG. 2. FIG. 2 shows that over preferred stroke length of 0-4 mm, a wide range of clamping forces can be obtained for each preset pressure used.

The grip also includes a force indicator 32 (shown in FIGS. 3a, b and c) that is seen through a window 33 (this can be seen in FIG. 4) on the main body 30. The purpose of this is to allow the user to easily check which force band the grip is working in. In normal use, it is unnecessary to know the clamping force. Although a general rule of thumb is for the clamping force to be about 2-3 times the maximum tensile load applied to the specimen, the general goal is simply to achieve effective specimen clamping with a minimum clamping force. The force indicator preferably comprises of three coloured band indicators of which they are red, green and white. Therefore, the coloured indicator is sufficient to provide the user guidance in usage.

Figure 4:
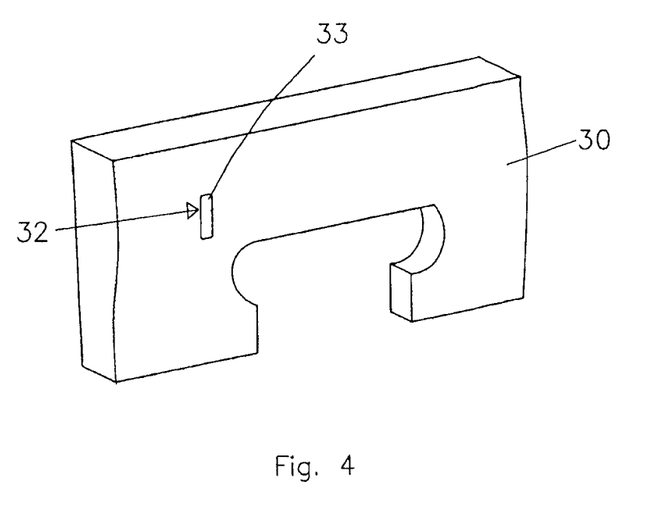
FIG. 4 is a perspective view of part of the powered grip illustrating the indicator.
Figure 5:
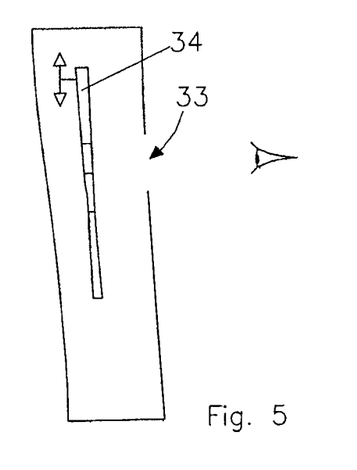
FIG. 5 is a sectional view through FIG. 5 at the indicator region to illustrate the features of the indicator.

FIGS. 3a, 3b and 3c show a partial hidden detailed view of the power grip in three different positions, representing the different coloured band indicators of the force indicator. FIG. 4 shows a perspective view of part of the grip 1 wherein a window 33 is shown through the main body 30. As shown in FIGS. 3a, b and c, the force indicator 32 is connected to the piston 2 through the grip body and cylinder 3. Therefore, as the piston 2 actuates down, the force indicator 32 moves together so that when the specimen is clamped and the clamping force is achieved, the piston 2 with the force indicator 32 will also stop and through the window 33, the force band colour may be observed that indicates the clamping force.

In general, operating with the grip in the red band would not be optimum as the grip will be close to its end of stroke (eg as shown to be close to in FIG. 3c) and may not have sufficient travel to accommodate any specimen contraction. Ideally the grip needs to operate in the green or white zone (as shown in FIGS. 3a and 3b). The white zone (shown in FIG. 3a) will indicate that the clamping force applied is at the low end of the possible range, while the green zone (shown in FIG. 3b) will indicate a higher clamping force and when the red zone is visible, the maximum range is being approached.

Figure 6:
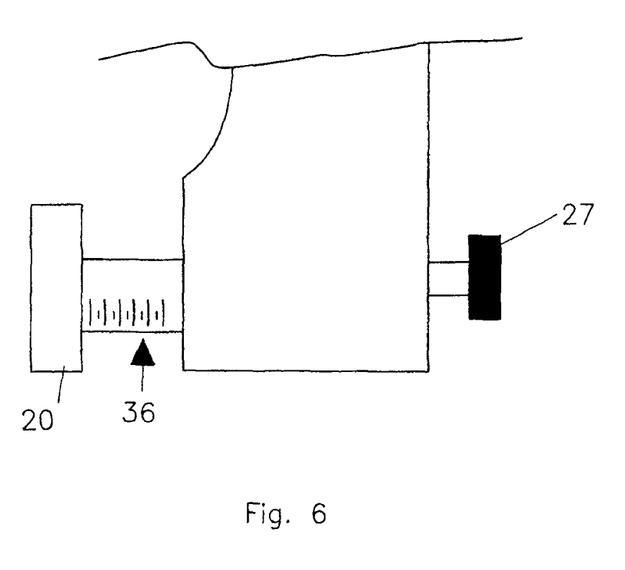
FIG. 6 is a close up side view of part of the powered grip of the present invention illustrating the graduated markings.

Each jaw mount such as jaw mount 22 as shown in FIG. 6 has a graduated scale 36 to assist in setting the desired jaw stroke for the appropriate clamping force. To setup, the user will manually turn the adjustment screw so that the jaws clamp onto the specimen using finger pressure. Then, noting the marking on the jaw mount, reverse the adjustment screw by the amount of jaw stroke length that is required. The amount of stroke length that is required is determined by first estimating the clamping force required, possibly by applying a 2 times multiple on the expected test load. So therefore one needs to choose the desired piston operating pressure (eg 5 bar) then choose the clamping pressure that will be needed (eg 20 kN) and then determine the jaw stroke that is needed (in this case corresponding to point 38 on FIG. 2, being around 3.6 mm) by reading off the clamping force chart. This then sets the free stroke of the jaws prior to them engaging onto the item to be clamped.

Accordingly, the grip of the present invention can allow for the deliberate varying of the force multiplier by virtue of simple mechanical settings at the grip. In addition to changing the cylinder pressure, by effectively adjusting the multiplier, the clamping force on the specimen can also be changed. So for a certain fixed cylinder operating pressure, the grip can generate a range of clamping forces as set by adjustment of the grip by the user.

Furthermore, the grip can also provide a progressive increase in clamping force so that as the specimen is being tested and reduces in thickness, the clamping force can also increase. The arrangement can also provide progressive increase in clamping force so that as the specimen is tested, the clamping force will also increase.

The invention allows tuning at the clamp jaws, in order to provide an optimal range of movement of the jaws yet still allows a wide range of clamping forces to be provided.

Adjustment allows (for different spacing of clamp jaws at initial contact with an item to be tested) the setting of the geometry of the force transmission mechanism (eg the lever, beam and jaw mount) in a condition so that, for a given operating pressure of the actuator, the multiplication of force remains within a range that corresponds to a desired range of clamping force.

Setting of a range of clamping force can now be done directly at the grip by the adjustment of the clamp jaws. This can be achieved by adjusting the stroke of the clamping jaws that clamp the specimen. Setting the clamping force can be done by a simple adjustment of the jaw face position against a graduated set of marks on the jaw face carrier and by means of the simple 3 color indicator.

So now the force multiplication ratio can have a range within which the user can setup for. This way the output clamping force can be varied by changing the lever multiplier of its piston force.

The user can have a wider range of clamping forces possible with any specific grip. This is important when testing different materials. It also provides the user with greater flexibility and a quick fine adjustment of the clamping force.

This invention differs from the current grips in the way a variable clamping force is designed to become a benefit. It removes the constraint by allowing the multiplication factor to be user adjustable thereby creating a grip that allows the user to control, at the grip, the clamping force on the test specimen. In addition, by means of a colour coded indicator, the user has the means of determining the approximate level of clamping force he is applying.

It is important to note that the grip design is primarily driven by 2 key parameters. The first is as stated, the ability to provide useful force multiplication in a compact design that is user adjustable at the grip itself and give some form of indication as to the level of clamping force. A second important factor is that the grip should also be self compensating when the specimen being clamped undergoes a reduction in thickness as a result of the applied load during a test. This is a primary reason for using powered grips compared to manual mechanical types. However, the grip in compensating for thickness changes should also result in an increase in clamping force rather than maintaining a constant or reduced clamping force. This benefit is important to prevent the specimen from slipping out of the grips.

Figure 8:
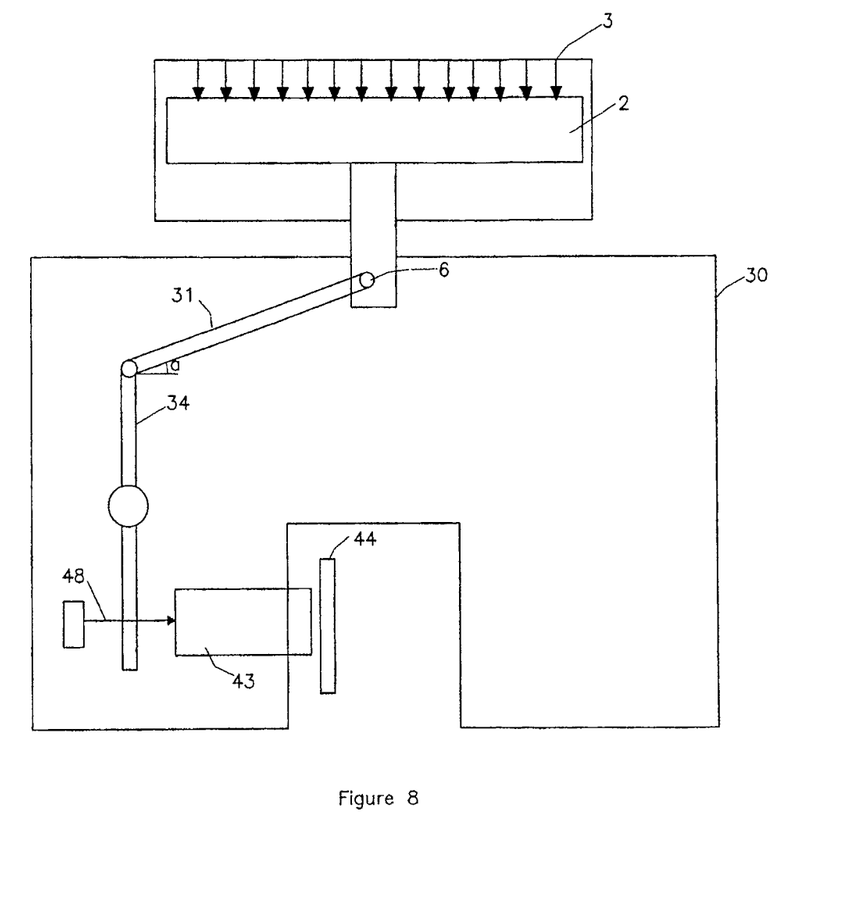
FIG. 8 is a schematic view of a power grip where only one clamp jaw moves relative to the housing.
Figure 9:
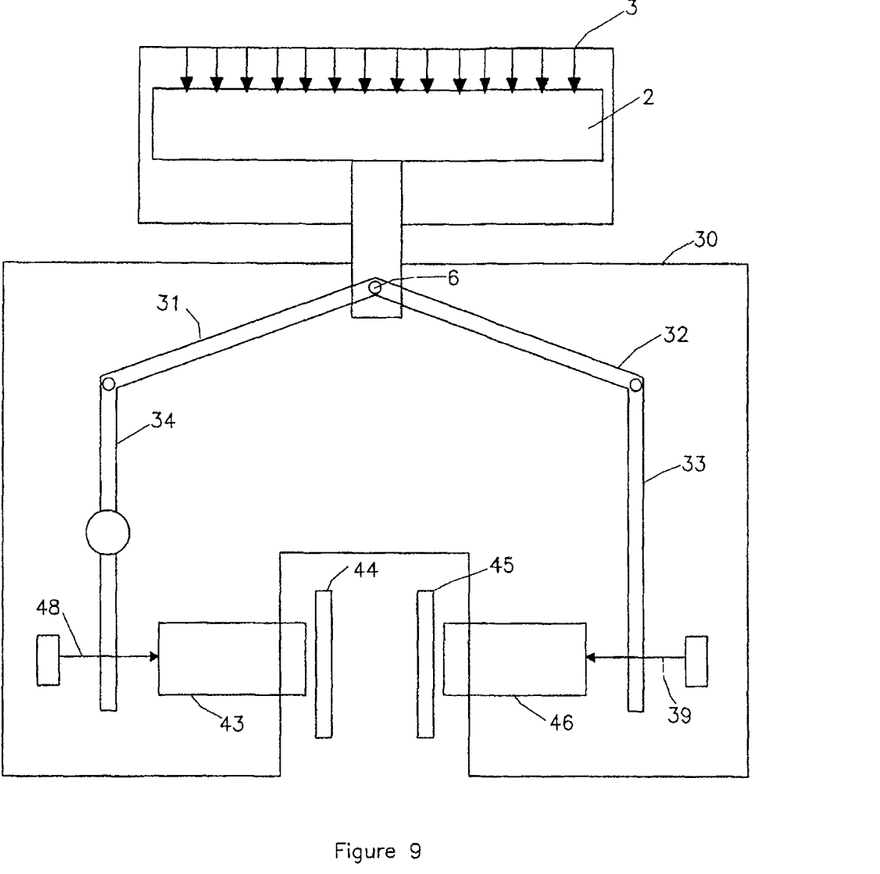
FIG. 9 is a schematic view of a power grip where both clamp jaws are adjustable with one side of the grip stationary.

FIGS. 8 and 9 show another preferred form of the invention where only one of the clamping jaws moves relative to the main body. The other stays stationary. The grip includes a main body 30 holding a piston 2 within a cylinder 3. As shown in FIG. 9, the piston acts (directly or indirectly) on two identical beams 32, 31 having a single hinged joint 6 connecting the piston 2 with the beams. It is preferable that the piston acts on the ends of these two beams 31, 32.

At the opposed end of the beams connecting the beams with the piston, each beam acts on a lever arm 33, 34. Beam 32 however, is preferably attached to lever 33 via a coupling that preferably locks the beam 32 and lever 33 into a configuration that is immovable or stationary. Alternatively, a single unitary construction of a beam 32 and a lever 33 may be used. In FIG. 9, the angle between beam 32 and lever 33 is the same as the angle 'a' as the opposed beam 31 and lever 34. However, a range of angles can be used as long as the beam and the lever are fixed and immovable. Since the right side of the grip comprising beam 32 and lever 33 are fixed and immovable, no moment forces are generated on the side that is stationary.

A jaw mount 46 may preferably be attached to the end of the immovable beam 33 and lever configuration as shown in FIG. 9 to allow for replacement of jaws when appropriate. Alternatively, the jaw mount 46 may also be formed as a unitary construction together with the beam and lever configuration. A clamp jaw 45 is attached at the end of the jaw mount. An adjustment mechanism 39 is also included in the jaw mount 46. This allows the spacing between the clamp jaws 44, 45 to be varied. Alternatively, the adjustment mechanism may not be included with the jaw mount and the clamp jaw 45 remains stationary relative to the main body.

The opposed beam 31 and lever 34 are preferably connected by a hinged coupling which allows for angle 'a' to be adjusted, similar to the previous embodiment as shown in FIG. 1. Intermediate of each lever arm between the distal ends 41, 42 is a pivot point. The lever arm 34 respectively act on clamp jaw 44 preferably via jaw mount 43. Similarly, a clamp jaw 45 is preferably attached via jaw mount 46 on the opposed beam and lever configuration. Since the beam and lever configuration are- fixed and immovable, a specimen may be located between the clamp jaws 44 and 45 and be subjected to a tensile force from the clamp jaw 44 by moving the clamp jaw 44 towards the fixed clamp jaw 45.

The jaw mount 43 includes an adjustment mechanism 48 which is similar to the adjustment mechanism 26 of FIG. 1. This mechanism allows the spacing of the clamp jaw 44 and 45 to be varied. In use, a specimen is located between the clamp jaws 44 and 45. An initial configuration of the grip by manipulating the adjustment mechanism is first obtained when the specimen is first engaged by the jaws. This ensures that the grip geometry operates within a range that is desirable. The jaw mount also includes a graduated scale to assist the setting of the desired jaw stroke for the appropriate clamping force.

In another embodiment of the invention as shown in FIG. 8, only the beam and lever configuration on one side of grip is included. This is similar to the beam 31 and lever 34 of FIG. 9. The jaw mount 43 also includes the adjustment mechanism 48 and clamp jaws 44. In this preferred embodiment, the clamp jaw 44 clamps the specimen against the main body 30.

Figure 10:
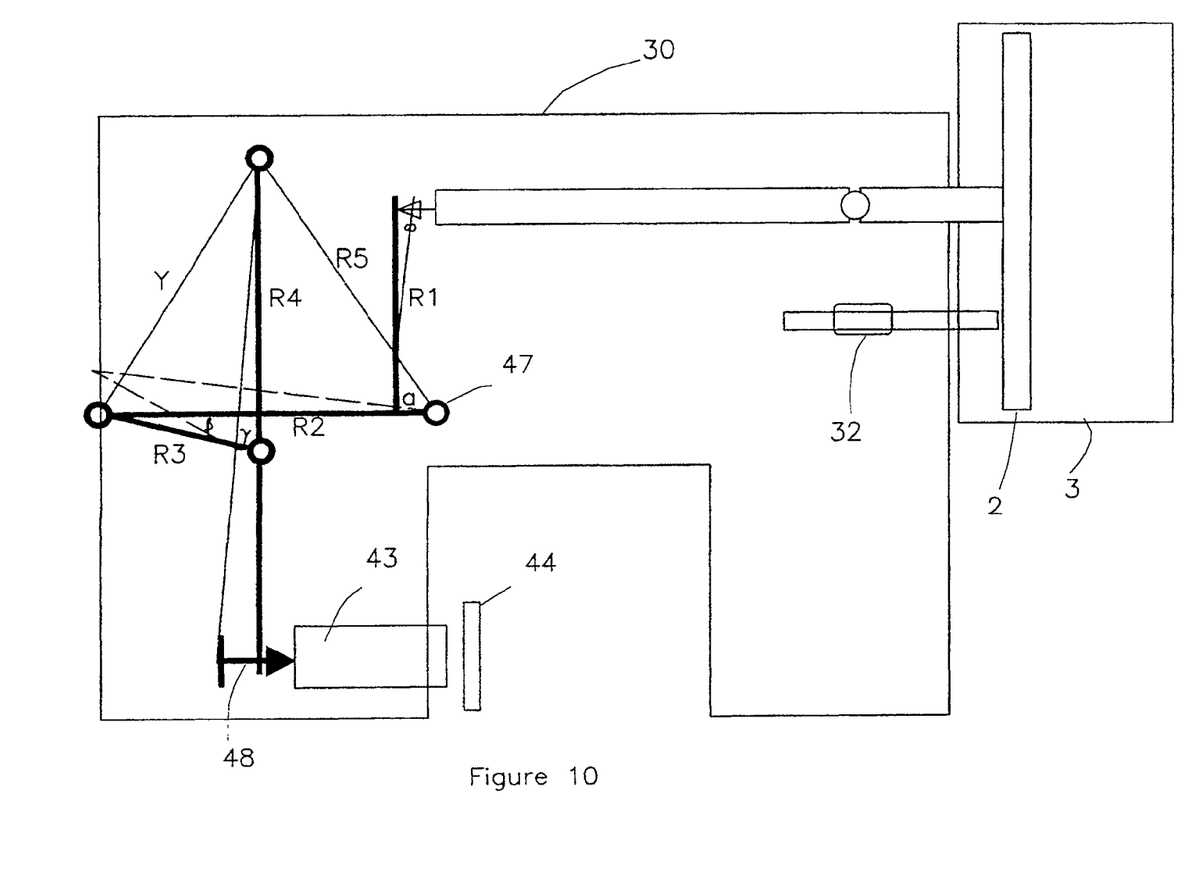
FIG. 10 is a schematic view of a power grip with a single sided clamp jaw linked lever configuration.

FIG. 10 shows another form of the invention where a single-side clamp jaw having a lever linked configuration clamps a specimen (not shown in the figure) on the main body 30 which is stationary. FIG. 10 also shows a lever linked configuration in two positions, one where the piston is at the start of the stroke (as shown in grey) and one where the piston is at the end of the stroke (as shown in bold).

As shown in FIG. 10, the piston 2 actuates in a direction opposed to the clamping force generated on the specimen. The piston 2 acts (directly or indirectly) substantially on one end of lever R1 which is linked via a hinged joint to lever R2. Levers R1 and R2 are rigidly joined at the opposed end of R1 where the piston acts and towards the end of lever R2, where lever R2 is substantially perpendicular to lever R1. The levers R1 and R2 will pivot around a hinged joint 47 upon activation by the piston on the end of lever R1. Therefore, the force generated by the piston 2 is translated to a thrust force to lever R1 which in turn is transferred to an associated lever arm R3.

The lever R2 and R3 forms an angle β. In use, as the angle β approaches 0, the lever R3 causes lever R4, which is joined to R3 by a hinge joint, to act on the clamp jaw 44 via the jaw mount 43. Therefore, the clamping force generated by the clamp jaw 44 from the lever linked configuration when the grip is in use is applied in a direction opposed to the force generated by the piston on the specimen. The specimen is clamped against the main body 30 on the opposed side of the clamp jaw 44.

In FIG. 10, the jaw mount 43 includes adjustment mechanism 48 which allows the spacing of the clamp jaw 44 and the opposed side of the main body 30 to be varied. It is noted that the main body 30 when in use remains stationary relative to the movement of the lever linked configuration. The jaw mount 48 has a graduated scale similar to the previous embodiment shown in FIG. 2. The graduated scale assists in setting the desired jaw stroke for the appropriate clamping force. Preferably, the grip also includes a force indicator which allows the user knowledge of the optimum clamping force on the specimen. The grip also includes a force indicator 32 as shown in FIG. 10. This feature is similar to the previous embodiments described and indicates to the user the optimum clamping force to be applied.

Where the grip is used in situations where material thickness of the jaws does not reduce (such as in compression testing) the advantage of the invention in relation to changing jaw clamping force in response to a reduction in material thickness at the jaws, will not be achieved.

The invention claimed is:

1. A powered grip for engaging and holding an item, said grip comprising:
   a primary body member,
   an actuator dependent from said primary body member,
   a pair of spaced apart clamp jaws movable towards and away from each other and configured to clamp onto said item,
   a force transmission mechanism coupling said actuator and said pair of clamp jaws to displace said clamp jaws relative the primary body and to establish, at the clamp jaws, a clamp force which is a multiplication of an actuator force of the actuator by a factor greater than zero,
   a force transmission mechanism geometry adjuster configured to adjust a geometry of the force transmission mechanism in order to vary a spacing between the clamp jaws to thereby, for a given actuator force applied by the actuator to the force transmission mechanism, allow a pre-clamping setting of the spacing between the jaws such that a range of the clamp force applied by the clamp jaws to the item to be clamped is within a desired range,
   wherein said force transmission mechanism includes at least one pivot point that remains fixed to said primary body member, and said force transmission mechanism is rotatable about the at least one pivot point in a manner to establish said multiplication of the actuator force at the clamp jaws.

2. The power grip as claimed in claim 1, wherein said actuator is one selected from the group consisting of (a) a piston and cylinder arrangement that is coupled to the transmission mechanism and displacement of the piston within the cylinder is effected by a fluid and (b) an electromechanical arrangement.

3. The power grip as claimed in claim 1, wherein said force transmission mechanism comprises, for each clamp jaw, a lever member pivotally mounted relative the primary body member and coupled to said clamp jaw, the lever member rotatable about a pivot in response to the actuator force to move said clamp jaw relative the other clamp jaw.

4. The power grip as claimed in claim 3, wherein said force transmission mechanism, for each clamp jaw, further comprises a link beam that couples the lever member with said actuator, said link beam coupled to said lever member to apply a moment to said lever member to cause the lever member to rotate about the pivot of the lever member, thereby transferring the moment by said lever member and as the clamp force to the clamp jaw.

5. The power grip as claimed in claim 4, wherein said force transmission mechanism further comprises, for each clamp jaw, a jaw mount, and
   for at least one of said clamp jaws, the jaw mount is configured to transfer the clamp force to the clamp jaw.

6. The power grip as claimed in claim 1, wherein said force transmission mechanism, for each clamp jaw, further comprises a jaw mount.

7. The power grip as claimed in claim 5, wherein the jaw mount is coupled to the lever member and the corresponding clamp jaw.

8. The power grip as claimed in claim 7, wherein said jaw mount is pivotally coupled to said lever member.

9. The power grip as claimed in claim 8, wherein said link beam and said jaw mount are pivotally coupled to said lever member on opposite sides of the pivot.

10. The power grip as claimed in claim 4, wherein said link beam is pivotally connected to said actuator and said lever member.

11. The power grip as claimed in claim 5, wherein said force transmission mechanism geometry adjuster is defined by said jaw mount that is adjustably mounted to said lever member in order to allow the spacing between the clamp jaws to be varied, without movement of the lever member.

12. The power grip as claimed in claim 5, wherein said force transmission mechanism geometry adjuster is defined by said jaw mount that is adjustable in size in order to allow the spacing between the clamp jaws to be varied, without movement of the lever member.

13. The power grip as claimed in claim 12, wherein said jaw mount comprises a first portion that remains secured to said lever member and a second position, held by said first portion in a movable relationship thereto.

14. The power grip as claimed in claim 13, wherein said first portion and said second portion are threadingly engaged with each other, such that upon relative rotation, a linear displacement between the two portions occurs to vary the spacing between the clamp jaws.

15. The power grip as claimed in claim 1, wherein said force transmission mechanism geometry adjuster is configured to allow, for different spacings of clamp jaws at initial contact with the item to be clamped, the setting of the geometry of the force transmission mechanism in a condition so that, for a given actuator force of the actuator, the clamp force remains within the desired range.

16. The power grip as claimed in claim 1, wherein the grip is adapted to be used for materials testing.

17. The power grip as claimed in claim 1, where the force transmission mechanism is arranged to provide a mechanical advantage.

18. The power grip as claimed in claim 1, wherein said factor is greater than 1.

19. A powered grip for engaging and holding an item, said grip comprising:
   a primary body member,
   an actuator dependent from said primary body member,
   a pair of spaced apart clamp jaws mounted from said primary body member in a manner to allow a distance between the clamp jaws to vary and each of the pair of clamp jaws being configured to clamp onto said item, a force transmission mechanism coupling said actuator and at least one of the clamp jaws of said pair of clamp jaws to displace said at least one clamp jaw relative the primary body to vary the distance between said clamp jaws and to establish, at the clamp jaws, a clamp force which is a multiplication of an actuator force of the actuator by a factor greater than zero, a force transmission mechanism geometry adjuster configured to adjust a geometry of the force transmission mechanism in order to vary the distance between the clamp jaws to thereby, for a given actuator force applied by the actuator to the force transmission mechanism, allow a pre-clamping setting of the distance between the jaws such that a range of the clamp force applied to the item to be clamped between the clamp jaws is within a desired range, wherein said force transmission mechanism includes at least one pivot point that remains fixed to said primary body member, and said force transmission mechanism is rotatable about the at least one pivot point in a manner to establish said multiplication of the actuator force at the clamp jaws.

20. The power grip as claimed in claim 19, wherein said force transmission mechanism comprises, for said at least one clamp jaw, a lever member pivotally mounted relative the primary body and coupled to said at least one clamp jaw, the lever member rotatable about a pivot in response to the actuator force to move said clamp jaw relative the other said clamp jaw.

21. The power grip as claimed in claim 19, wherein said force transmission mechanism further comprises a link beam that couples the lever member with said actuator, said link beam coupled to said lever member to apply a moment to said lever member to cause the lever member to rotate about the pivot of the lever member, thereby transferring the moment by said lever member and as the clamp force to the clamp jaw.

22. The power grip as claimed in claim 19, wherein said force transmission mechanism geometry adjuster further comprises a jaw mount which is configured to transfer the clamp force to the at least one clamp jaw.

23. The power grip as claimed in claim 22, wherein said force transmission mechanism comprises, for said at least one clamp jaw, a lever member pivotally mounted relative the primary body, and
said force transmission mechanism geometry adjuster comprises said jaw mount that is adjustably mounted to said lever member in order to allow the distance between the clamp jaws to be varied, without movement of the lever member.

24. The power grip as claimed in claim 22, wherein said force transmission mechanism geometry adjuster comprises said jaw mount that is adjustable in size in order to allow the distance between the clamp jaws to be varied, without movement of the lever member.

25. The power grip as claimed in claim 19, wherein the force transmission mechanism further comprises a combination of lever members mechanically linked to couple with said actuator, said combination of lever members configured to apply a moment to at least one of the lever members to cause the at least one of the lever members to rotate about the pivot of one of the lever members, thereby transferring the moment by said at least one of the lever members and as the clamp force to the clamp jaw.

26. The power grip as claimed in claim 19, wherein the grip is adapted to be used in materials testing.

27. The power grip as claimed in claim 25, wherein said combination of lever members comprises
a first lever member, a first end of which is coupled to the actuator,
a second lever member, a first end of which is joined to a second end of the first lever member,
a third lever member having a first end pivotally coupled to the second lever member, a fourth lever member having a first end pivotally coupled to the primary body member for allowing the combination of lever members to apply a moment to the fourth lever member to cause the fourth lever member to rotate about said first end of the fourth lever member, and the third lever member having a second end joined to a midpoint of the fourth lever member,
wherein when the actuator actuates, the combination of lever members applies the moment as the clamp force to the clamp jaw.

28. The power grip as claimed in claim 27, wherein the first and second lever members are rigidly connected to each other.

29. The power grip as claimed in claim 28, wherein the first end of the second lever member member is coupled to the primary body member via a hinge joint.

30. The power grip as claimed in claim 29, wherein the second lever member is not in contact with the fourth lever member.

31. A powered grip for engaging and holding an item to be clamped, said grip comprising:
a primary body member,
an actuator dependent from said primary body member,
a pair of spaced apart clamp jaw mounts, each of the clamp jaw mounts for receiving a clamp jaw being movable towards and away from each other and configured to allow the clamp jaws, when mounted, to clamp onto said item,
a force transmission mechanism coupling said actuator and the clamp jaw mounts to establish, at the clamp jaws, a clamp force which is a multiplication of an actuator force of the actuator by a factor greater than zero,
a force transmission mechanism geometry adjuster configured to adjust a geometry of the force transmission mechanism independently of movement of the force transmission mechanism in order to vary a spacing between the clamp jaw mounts to thereby, for a given actuator force applied by the actuator to the force transmission mechanism, allow a pre-clamping setting of the spacing between the jaws such that a range of the clamp force applied by the clamp jaws to the item to be clamped is within a desired range.

32. A method of clamping an item by utilising the power grip as claimed in claim 1, comprising setting the clamp jaws a determined distance apart before actuating the actuator to move the clamp jaws towards each other.

33. The method as claimed in claim 32, wherein the determined distance sets a free stroke of the clamp jaws and the force transmission mechanism, and sets the geometry of the force transmission mechanism upon initial clamping of the item.

34. A powered grip for holding an item to be tensile tested, said item is susceptible to a size reduction when under tension at a location where the item is to held by the powered grip, said grip comprising:
a primary body member,
an actuator dependent from said primary body member,
a pair of spaced apart clamp jaws movable towards and away from each other and configured to clamp onto said item, a force transmission mechanism coupling said actuator and said pair of clamp jaws to displace said clamp jaws relative the primary body member and to establish, at the clamp jaws, a clamp force which is a multiplication of an actuator force of the actuator by a factor greater than zero, a force transmission mechanism geometry adjuster configured to adjust a geometry of the force transmission mechanism independently of movement of the force transmission mechanism in order to vary the spacing between the clamp jaws to thereby, for a given applied by the actuator to the force transmission mechanism, allow a pre-clamping setting of the spacing between the jaws such that a range of the clamp force applied by the clamp jaws to the item to be clamped is within a desired range so that when the item, under tensile loading, decreases in size at the clamp jaws, the clamp jaws move to compensate for the size reduction and by virtue of the change in the geometry of the force transmission mechanism, increase the clamp force.

* * * * *